United States Patent [19]

Ricci

[11] Patent Number: 5,759,035
[45] Date of Patent: Jun. 2, 1998

[54] BONE FUSION DENTAL IMPLANT WITH HYBRID ANCHOR

[76] Inventor: Fernando Ricci, Via T Dacelano #41 Int 26, 00179 Rome, Italy

[21] Appl. No.: 696,252

[22] Filed: Aug. 13, 1996

[30] Foreign Application Priority Data

Nov. 3, 1995 [IT] Italy ................... RM95A0728

[51] Int. Cl.$^6$ ........................................ A61C 8/00
[52] U.S. Cl. .......................................... 433/174
[58] Field of Search ........................... 433/172, 173, 433/174, 175, 176

[56] References Cited

U.S. PATENT DOCUMENTS

| | | | |
|---|---|---|---|
| 4,431,416 | 2/1984 | Niznick | 433/174 |
| 4,713,004 | 12/1987 | Linkow et al. | 433/174 |
| 5,078,607 | 1/1992 | Niznick | 433/174 |
| 5,209,659 | 5/1993 | Friedman et al. | 433/174 |
| 5,312,256 | 5/1994 | Scortecci | 433/174 |
| 5,324,199 | 6/1994 | Branemark | 433/174 |
| 5,338,197 | 8/1994 | Kwan | 433/174 |
| 5,344,457 | 9/1994 | Pilliar et al. | 623/16 |

*Primary Examiner*—Nicholas D. Lucchesi
*Attorney, Agent, or Firm*—Ernest D. Buff

[57] ABSTRACT

Bone fusion dental implant of the type able to form an artificial dental root as a support for a fixed prosthesis composed of one or more dental crowns, said implant being inserted into the bone of the upper or lower jaw by drilling a hole at a suitable location and to which implant the surrounding bone tissue fuses permanently as it grows, said implant also having a substantially cylindrical shape, with a crown end (3) provided with means (11, 4) for connecting with a prosthetic reconstruction and an apical end (2) designed for insertion into the bone, said implant having an externally threaded section (6) extending from crown end (3) over no more than one-third of the entire length of the implant, and a s section (1) without an external thread extending from apical end (2) over no less than twothirds of said length. In the section (1) not threaded externally, the implant is coated with a bioactive material, preferably hydroxyapatite, and is surface-threaded to make it rough and/or porous.

16 Claims, 8 Drawing Sheets

BONE FUSION DENTAL IMPLANT WITH HYBRID ANCHOR

BACKGROUND OF THE INVENTION

1. Field Of The Invention

The present invention relates to a bone fusion dental implant with a hybrid anchor. More specifically, the invention relates to an implant able to constitute an artificial dental root, supported by a fixed prosthesis comprised of one or more dental crowns, which is inserted into the bone of the upper or lower jaw by drilling a hole at a suitable location and to which the surrounding bone tissue fuses permanently as it grows.

Bone fusion dental implants are composed of generally cylindrical elements of dimensions such that they can be accommodated firmly in the dental crest in the toothless area concerned and can withstand the mechanical forces transferred to them through the connected dental crowns by chewing. This connection is normally made by providing around the implant a coaxial cavity, with internal threads and open at the crown end of the implant, into which, after a suitable period of time during which the implant is left unloaded to allow proper fusing of the bone, the prosthesis element is screwed, possibly with interposition of intermediate elements.

The most widespread bone fusion implants in current use are divided into two major categories according to the method of anchoring to the bone in which the implant is inserted. One type is comprised of an external thread by which the implant is firmly screwed into the bone, while a second type consists of a substantially cylindrical body accommodated in the surgical cavity by inserting it axially then completing its positioning by percussion.

In both cases, the application procedure begins with making a first hole in the bone in the appropriate position and with the appropriate orientation, then enlarging the pilot hole to increasing diameters until the desired diameter is reached. At this point, insertion of a cylindrical implant by percussion requires only a few simple steps which consist of introducing the implant into the hole and striking it with a suitable hammer, with interposition of a suitable instrument to cause it to penetrate for the final distance. With a screwed implant, on the other hand, it is necessary to tap the bone unless implants of the self-threading type are used, and either the tapping or insertion of the implant must be done very slowly because overheating of the bone tissue breaks down its protein component leading to necrosis with consequent loss of the ability of the bone to fuse to the implant.

For both types of implant, the material of choice in terms of mechanical properties and compatibility with bone tissue is titanium, possibly alloyed with other elements. To speed up the process of bone fusion, particularly in the case of cylindrical percussion implants, coatings of bioactive material are provided, primarily hydroxyapatite, which has the same chemical composition as human bone and a porous surface structure, and is highly suitable for favoring growth of bone tissue in intimate contact with it. Surface treatments of the titanium element rendering it rough and porous, such as grit blasting and plasma spraying, have a similar effect.

In the case of cylindrical percussion implants, to favor anchoring to the bone and to cause the implant to withstand the twisting forces generated during the prosthetic procedures, axial blind holes, slits, or grooves are provided to interrupt the regularity of the cylindrical surface and later encourage occupation by newly grown bone tissue.

One example of the screw-type implant is described in European Patent Publication No. 0 343 135 (The Institute For Applied Biotechnology) which represents a further development of the original Branemark implant, the first known version of the bone fusion implant. Like the preceding implants, it has a cylindrical element with external threads for the greater part of its length, with a head portion at the crown end from which extends an internally threaded blind coaxial hole for connection with the prosthesis element. The head is slightly widened and constitutes a flange above which is provided with a portion in the shape of a hexagonal nut designed to engage a corresponding cavity with a hexagonal section in the prosthesis element to prevent relative rotation of the two elements.

Examples of cylindrical percussion implants are illustrated in European publication No. 0 370 590 (IMZ-Fertigungs und Vertriebsgesellschaft fur dentlale Technologie mbH) and in U.S. Pat. No. 5,316,476 (J. T. Krauser). The former represents a further development of the original IMZ implant which relates in particular to an intermediate structure made of plastic to be mounted between the implant and the crown installed thereon, but which illustrates the fundamental characteristics of the basic implant. The latter is comprised of a cylindrical element in which the apical hemispherical end and the crown end are provided with an internally threaded blind coaxial hole and having, at the apical end, two parallel slits passing through the cylindrical body, properly rounded at the edges.

The implant described in U.S. Pat. No. 5,316,476 is also cylindrical, with the frustroconical apical end and four axial grooves with rounded edges instead of through slits. Indeed, it has recently been demonstrated (see for example M. S. Block et al., Loaded Hydroxyapatite and Grit-Blasted Titanium Implants on Dogs, *The International Journal of Oral and Maxillofacial Implants*, Vol.4, pages 219–225) that the newly formed bone rarely occupies a through hole fully so that this function can be assumed by recesses rather than slits in the cylindrical surface. The crown end of the implant can be enlarged in a flange and surmounted by a hexagonal head, or, if sufficient bone thickness is available, the diameter of the implant can be increased until the flange is incorporated and accordingly disappears, leaving only the hexagonal head connected directly with the cylindrical body. According to other variants, the hexagonal head can be replaced by a widened cavity created at the entrance to the threaded hole. In order to promote rapid bone fusion, the surface of the implant below the flange, when present, or below a thin cylindrical crown strip when the flange is absent, is coated with a bioactive material or treated with titanium plasma or by other procedures rendering it sufficiently rough or porous.

It has been experimentally demonstrated (A. B. Carr et al., Reverse Torque Failure of Screw-Shaped Implants in Baboons: Baseline Data For Abutment Torque Application, The International Journal Of Oral and Maxillofacial Implants, Vol. 10, pages 176 [sic]–173) that surfaces coated with bioactive material or treated as already described achieve faster bone fusion which peaks as early as the end of the first three months while the untreated or uncoated titanium surfaces achieve maxium bone fusion in the fourth three-month period.

On the other hand, it has also been found that a reabsorption cone is ofter created around the implant due to initial bone retraction so that it is possible for a small crown area to remain uncovered. If the surfaces are exposed to the environment of the mouth as a consequence of initial bone retraction, the rough surfaces such as those coated with bioactive material or treated in some other way have distinctly inferior behavior with respect to the untreated surfaces, retaining more bacterial plaque and thus more easily giving rise to inflammatory phenomena with consequent eventual bone loss.

It can be seen from the above that both the macroscopic configuration and the surface configuration of the implants cited have both advantageous features and typical drawbacks, which offset each other. In fact, cylindrical percussion implants are inserted by a simpler and faster surgical procedure, while screwed implants take longer to insert, thus causing greater trauma to the bone tissue and the patient; on the other hand, the latter implants, because of the flights of the screw, offer primary (and hence immediate) stability which is far superior to that offered by cylindrical implants, and many studies demonstrate that this is crucial for achieving bone fusion. As far as the surfaces are concerned, coating with bioactive materials and roughening speed up the bone fusion process considerably but render any exposed parts more vulnerable to bacterial attack.

Hence, the goal of the present invention is to furnish a bone fusion dental implant that combines the best features of cylindrical implants and screwed implants as well as of coated and uncoated surfaces, allowing both easy insertion and firm anchoring to the bone from the outset, and favoring both rapid bone fusion and good resistance to attack by bacterial plaque.

For this purpose, the invention proposes a dental implant of the hybrid type which, in the portion at the crown end, has the characteristics of a screwed implant, being provided with an external thread extending for several flights, and toward the apex has the characteristics of a cylindrical percussion implant, being unthreaded and coated with a suitable bioactive material, or roughened or rendered porous on the surface. By means of this configuration, the implant can be easily installed by axial insertion as in the case of a cylindrical implant for part of its length, with insertion being completed by a screwing motion of only the final part, so that only a few turns are made. Since the densest region of the bone is precisely in the surface area (bone cortex) screw insertion through this layer only will provide as firm a connection as that of a normal screwed implant, and hence optimum primary stability, with far less trauma to the bone tissue, which is traversed by the thread for only a short distance at the surface. On the other hand, the rough or bioactive coating provided in the cylindrical part of the implant will ensure rapid bone fusion, shortening waiting times by comparison to those for uncoated or untreated implants. As used herein the term "bone fusion" means osseo integration.

Hence a specific object of the present invention is a bone fusion dental implant, substantially cylindrical in shape and having a crown end provided with means for connection with a prosthetic reconstruction and an apical end intended for insertion into the bone of the upper or lower jaw, and made of and/or coated with material compatible with the bone tissue, characterized in that it comprises an externally threaded section extending from said crown end over no more than one-third of the entire length of the implant, and a section without external threads extending from said apical end over no less than two-thirds of the entire length of the implant, said section being coated externally with a bioactive material or surface-treated so that it is rough and/or porous.

Preferably, the externally threaded section has no more than three or four flights of the self-threading type and the connection means include, as usual, a blind hole coaxial with the implant, open at the crown end and threaded internally, into which the prosthesis element is screwed, possibly by means of one or more intermediate elements.

To improve the resistance to twisting forces, two or more lengthwise grooves are preferably provided in the cylindrical part of the implant, said grooves having a round cross section and two ends which are also round. According to a specific embodiment of the invention, the grooves are two in number, diametrically opposite each other, and terminate at their apical ends in a hole passing through the implant, which hole is circular or at least has rounded ends.

As in most known cases, the material from which the implant is made is titanium or one of its alloys, and the cylindrical section extending from the apical end is preferably coated with hydroxyapatite or titanium plasma.

Further structural characteristics and advantages of the hybrid dental implant according to the invention will become evident by referring to several specific embodiments thereof shown as examples in the attached drawings, wherein.

Figure 1:
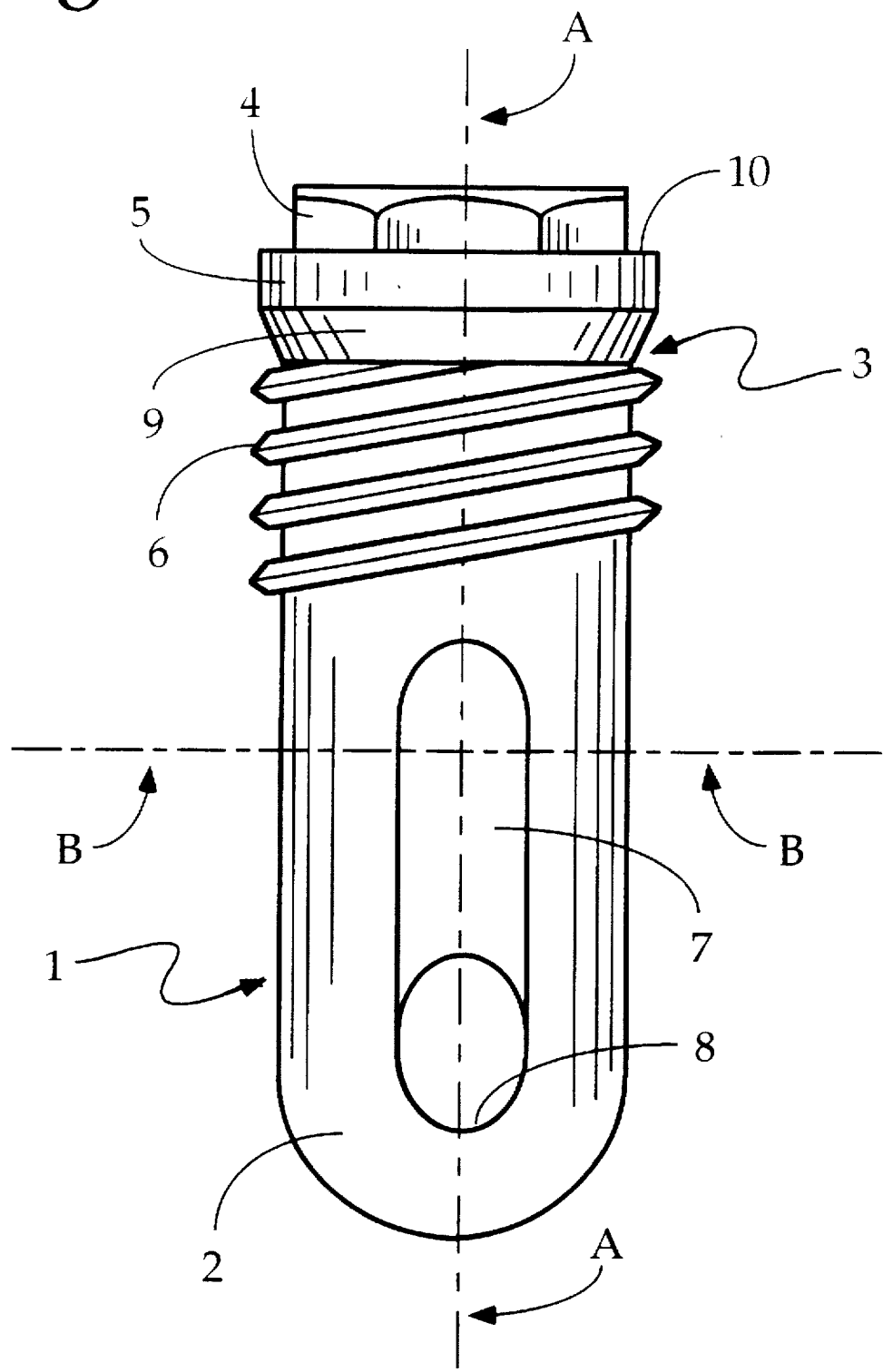
FIG. 1 shows a side elevation of a first implant form according to the invention.

The dental implant shown in FIGS. 1 to 4 comprises a substantially cylindrical portion 1 which extends over about two-thirds of the entire length of the implant (apical third and middle third) and ends in hemispherical apical end 2 and a crown portion 3 extending over no more than one-third of the length of the implant, said portion having a hexagonal head 4, a flange 5, and an externally threaded portion 6. Cylindrical portion 1 has on its surface two opposite lengthwise grooves 7 which are fairly wide and shallow and terminate at apical end 2 in a through hole 8 and extend over much of the middle third and apical third of the implant.

Flange 5 also covers the surface of the cylindrical body of the implant and connects to it by means of a frustroconical transitional area 9. Flange 5 has a flat surface 10 which surrounds hexagonal head 4, said surface providing adequate support for the prosthesis element (not shown) that will be supported by the implant. Immediately below frustroconical area 9 several self-threading flights of a screw thread begin that constitute externally threaded portion 6. This portion does not extend beyond the boundary between the crown third and the middle third of the implant.

The connection with the prosthesis element is accomplished by means of internally threaded blind hole 11 which receives a connecting screw and ends with said hexagonal head 4. As already noted, the hexagonal shape of head 4 is such as to prevent relative rotation between the implant and the prosthesis element, which is in turn provided with a recess able to engage hexagonal head 4 rotatably.

The implant illustrated in FIGS. 1 to 4 is made of titanium or one of its alloys; the crown third, including head 4, flange 5, and externally threaded portion 6, is not coated or treated in any particular way so that its surface is substantially smooth, while the middle third and the apical third, including substantially cylindrical portion 1 and apical end 2, are coated with hydroxyapatite. Consequently, while bone growth is favored by the presence of the hydroxyapatite coating, in the event of partial exposure to the environment of the mouth due to initial bone retraction, the implant will not offer a surface subject to attack by bacterial plaque.

The implant is inserted after preparation of a cylindrical hole in the bone Cf the upper or lower jaw by known drilling techniques. The implant is then inserted by an extremely simple and nonaggressive procedure, inserting it by the apical end 2 and pushing it to the bottom until the entire cylindrical portion 1 penetrates into the bone. At this point a screwing movement is executed until the entire implant including the crown third, penetrates the bone structure. The presence of an extremely small number of flights means that only a small number of rotations is necessary for complete insertion of the implant, with a consequent considerable reduction in surgical trauma. As already noted, there are enough flights to guarantee excellent primary stability without which bone fusion would not take place, since at the end of the insertion said flights are within the bone cortex.

Figure 2:
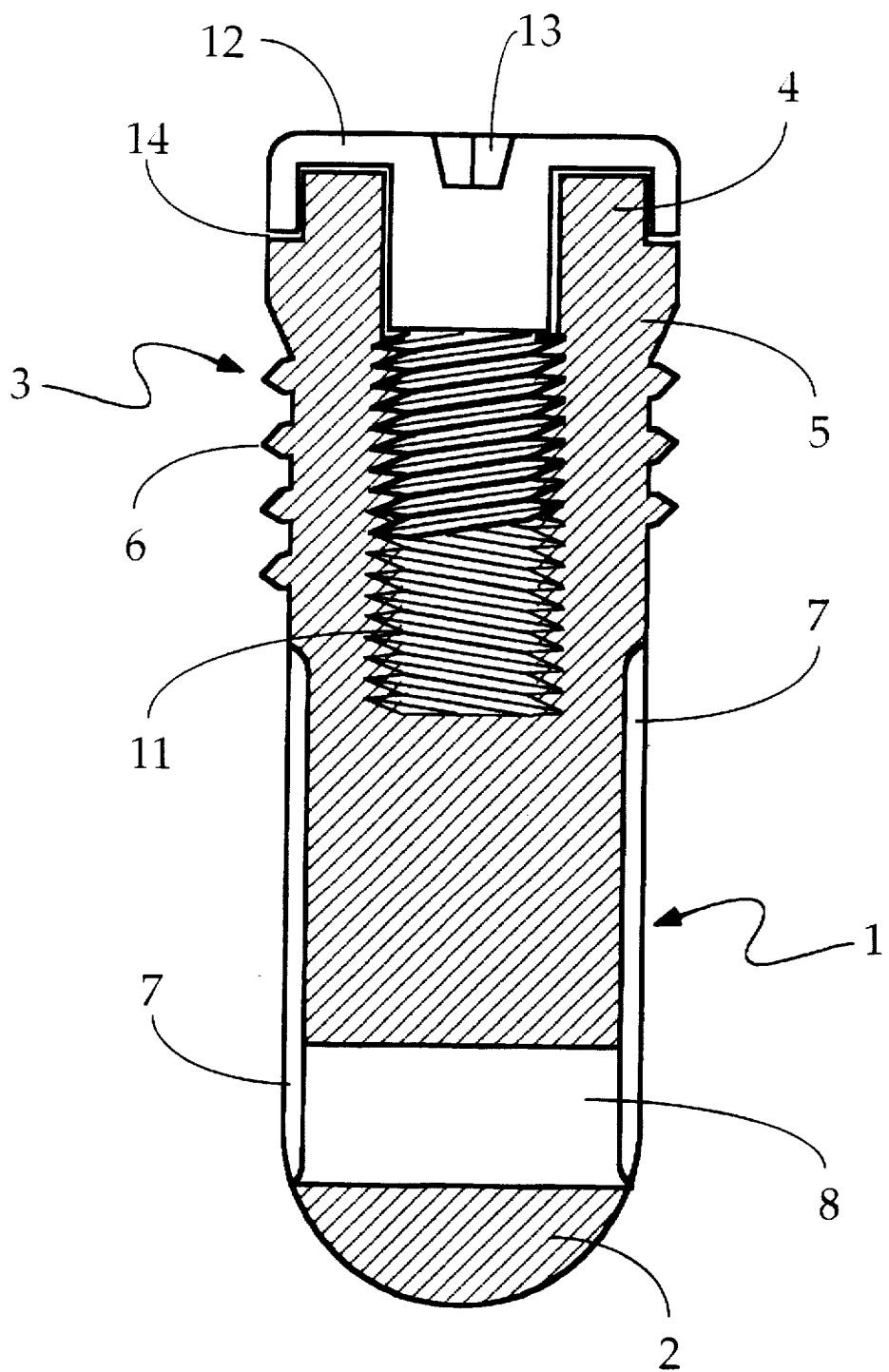
FIG. 2 is a view in axial section of the same implant taken along line A–A in FIG. 1 with the addition of a cover screw.
Figure 3:
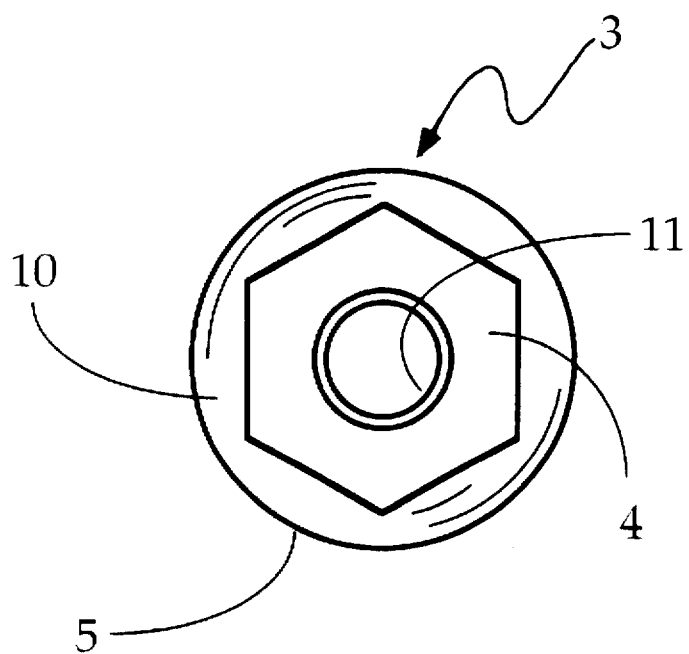
FIG. 3 is a plan view of the top of the implant in FIG. 1.
Figure 4:
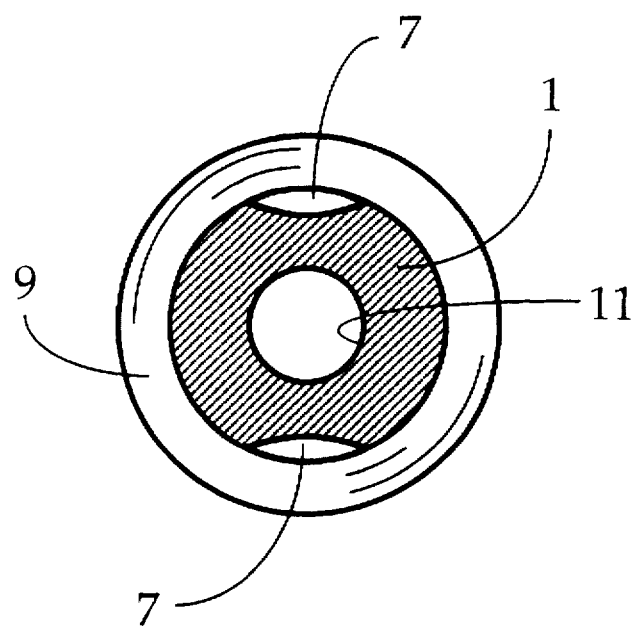
FIG. 4 is a cross-sectional view of the same implant as in FIG. 1, taken along line B—B.
Figure 5:
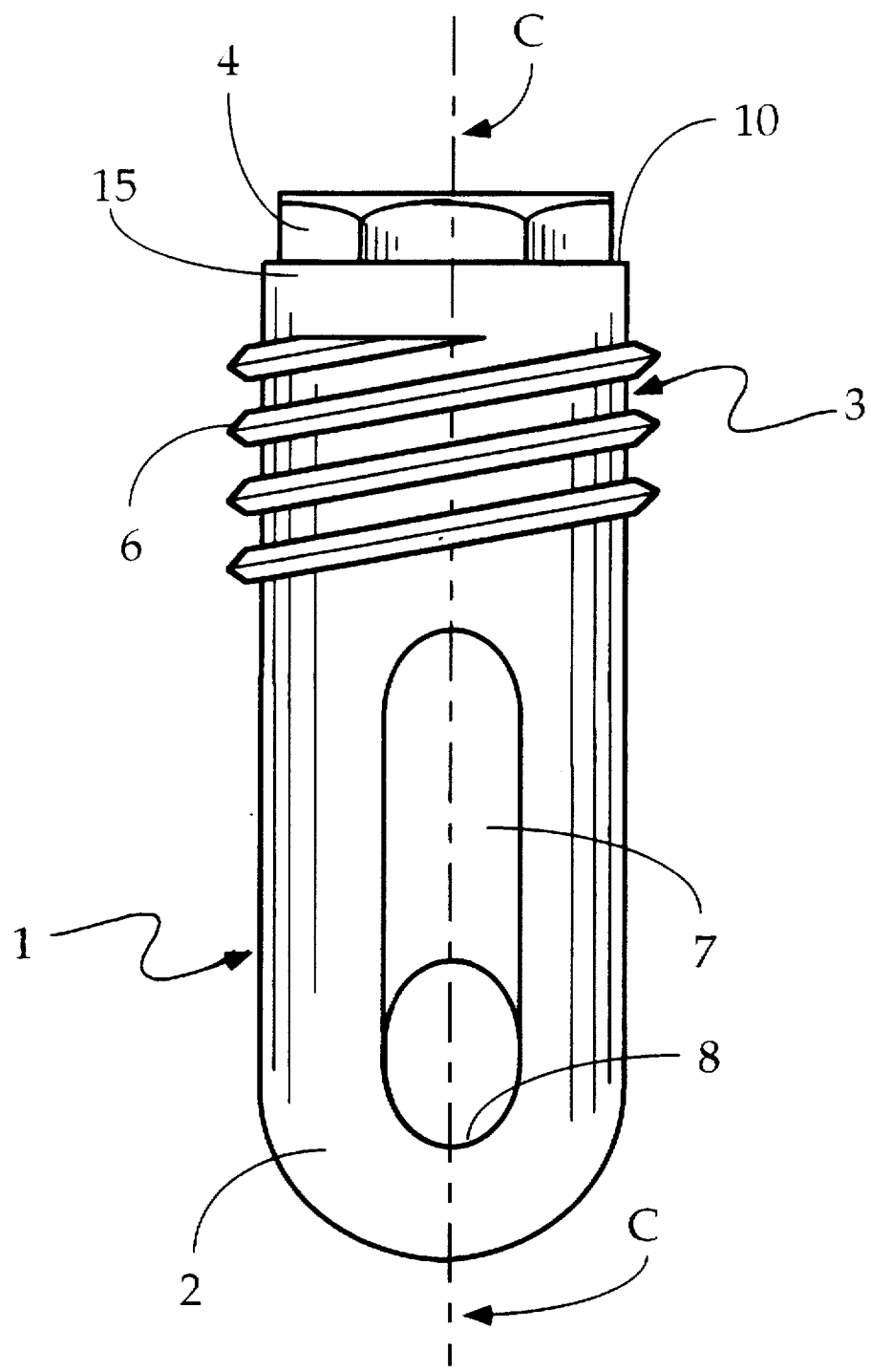
FIG. 5 is a side elevation of a second implant form according to the invention.
Figure 6:
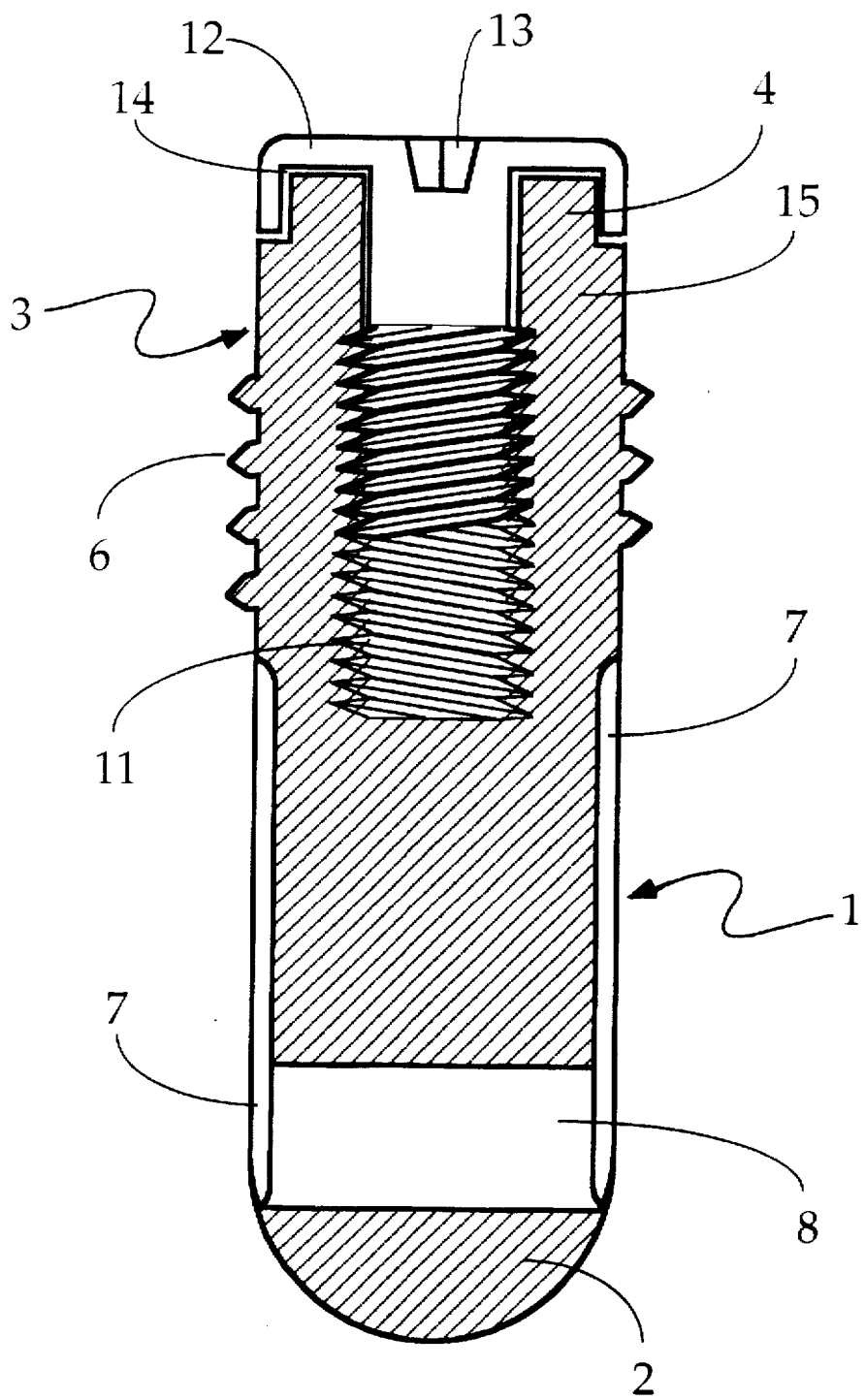
FIG. 6 shows an axial section of the same implant taken along the line CC in FIG. 5 with the addition of a cap screw.

During a period of time that allows the newly formed bone to reach the surface of the implant (this is known to be approximately three months due to the fact that the middle and apical thirds of the implant are surface-coated with hydroxyapatite), cap screw 12 is held on the implant as shown in FIG. 2 and has on its upper surface a cavity 13, preferably hexagonal and suitable for insertion of an Allen wrench, which both holds and turns screw 12. Cavity 13 tapers slightly downward such that the Allen wrench can fit flush, affording a firmer grip and more secure movement. Cap screw 12 has on its lower surface a cavity 14 in the form of a circular crown able to receive hexagonal head 4 of the implant in order completely to close blind hole 11.

At the end of the bone fusion period, when the dental implant is able to support the forces transmitted by chewing, cap screw 12 is removed after incision of the overlying oral mucosa, and a dental prosthesis is applied by connecting it to hexagonal head 4 in a manner already indicated.

Once bone fusion has occurred, lengthwise grooves 7 and through hole 8 have the dual function of stabilizing the dental implant against the rotary forces applied when the prosthetic connection is made and the extractive forces created by chewing sticky foods. In addition, the presence of grooves 7 and through hole 8 increases the surface of the bone/implant interface and furnishes an optimum geometry for transferring forces to the adjacent bone.

In the two dental implants shown in FIGS. 5–6 and 7–8, similar to the foregoing, similar structural elements are indicated by the same reference numerals. The first of the two variants illustrated shows an embodiment in which the entire implant has a constant diameter and flange 5 is absent, while hexagonal head 4 continues to be present. Between surface 10 to which the prosthesis is applied and the beginning of externally threaded portion 6 is a smooth cylindrical section 15 whose axial length is no more than one-eighth of the entire length of the implant, thus avoiding exposure of the threaded portion in the event of possible bone retraction. This version of the implant according to the invention later simplifies surgery by eliminating the necessity of creating in the bone a recess for flange 5, present in the first version.

Figure 7:
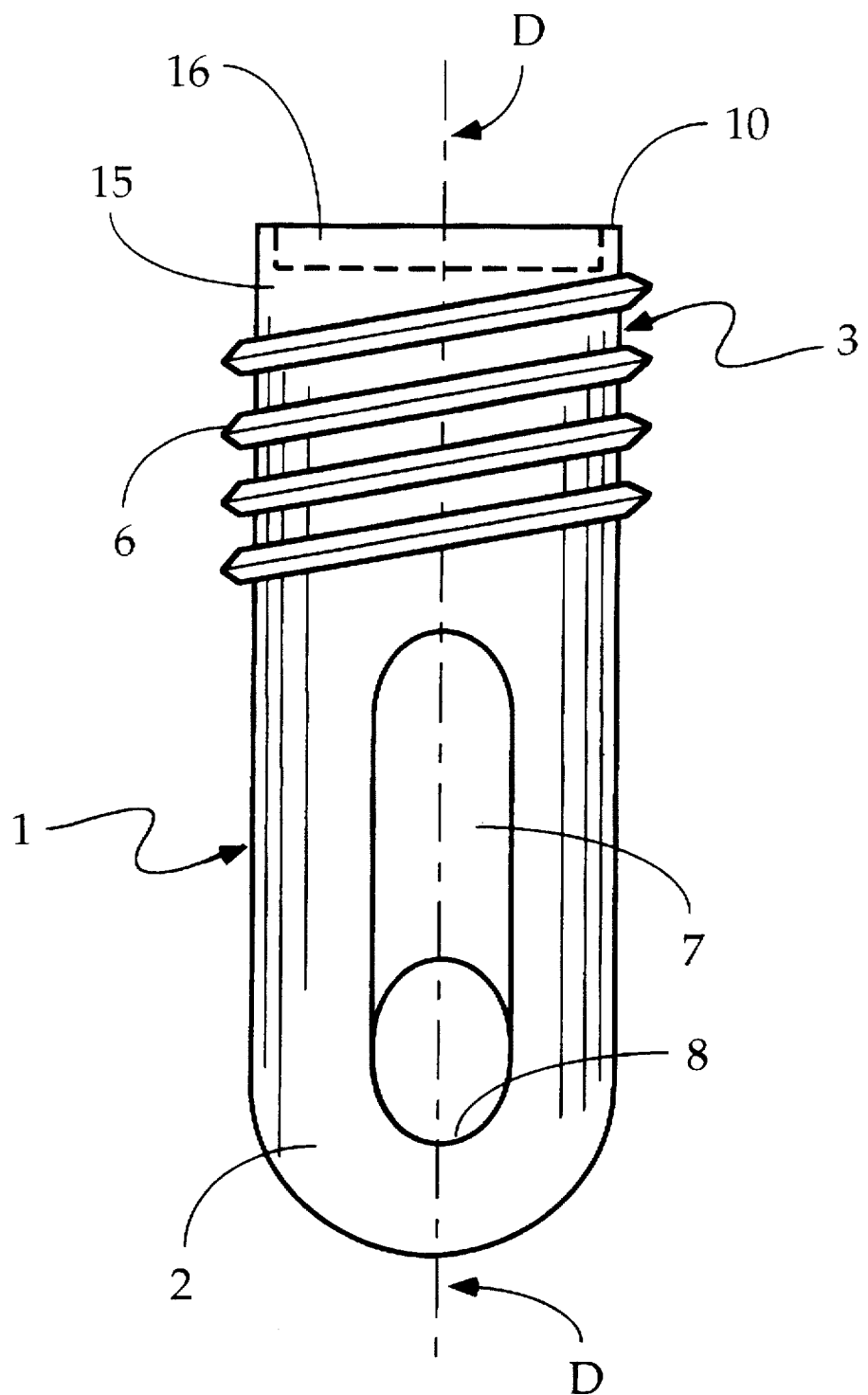
FIG. 7 shows a side elevation of a third implant form according to the invention.
Figure 8:
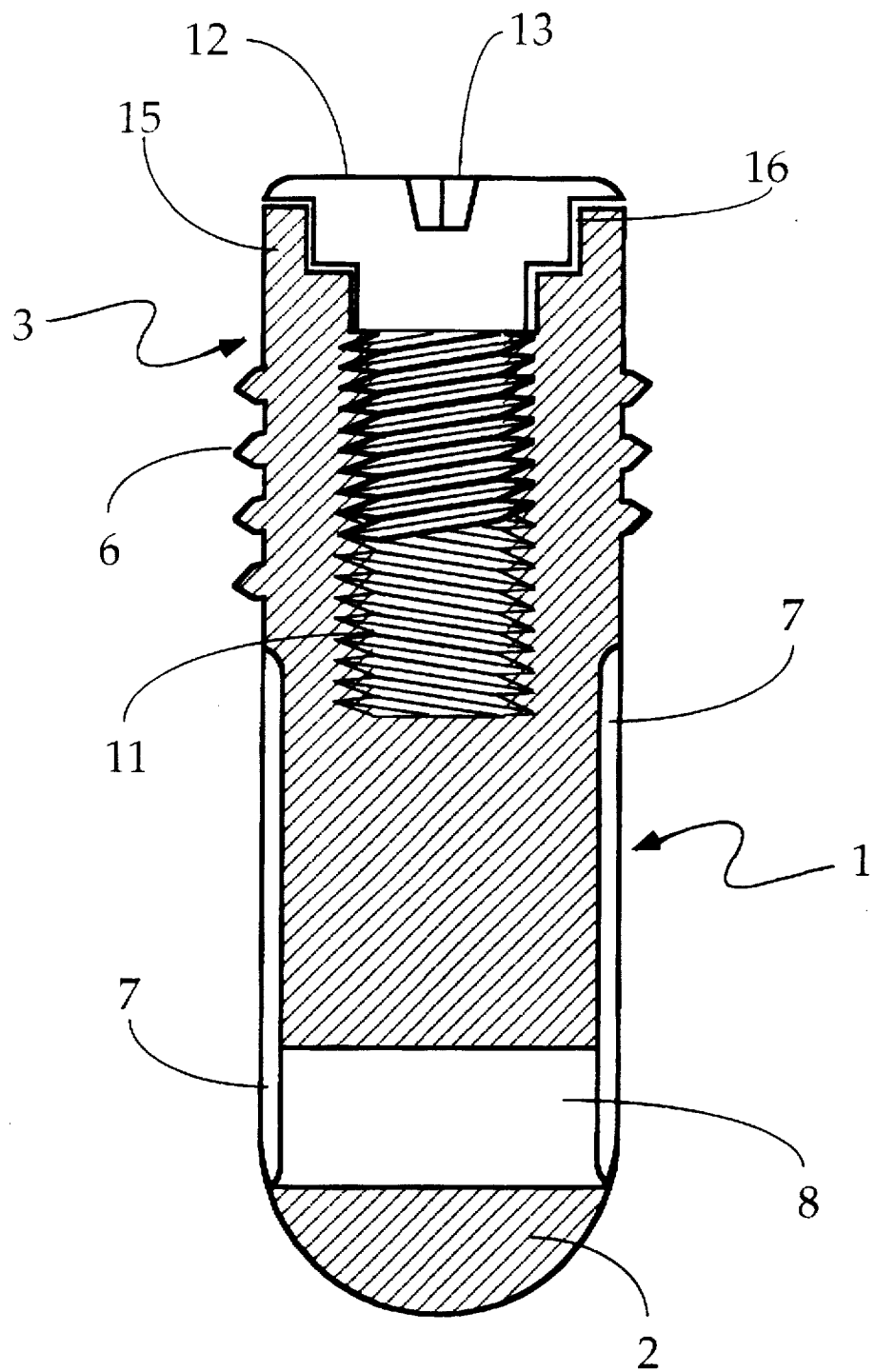
FIG. 8 shows an axial section of the same implant taken along line D—D) in FIG. 7 with the addition of a cap screw.

The variant illustrated in FIGS. 7 and 8 is of constant diameter like the previous variant and in addition has at the crown end a recess 16 of hexagonal shape in addition to hexagonal head 4 (shown in FIGS. 1–6). This variant lends itself better to the solution of esthetic problems where,
because of a considerable angle between the implant and the prosthetic restoration, the external hexagonal block would invade the restoration itself, altering its emergence profile. In the version illustrated, cap screw 12, which is not intended to cover a projecting hexagonal head, is not provided with a recess in the shape of a circular crown but: can have a step 17 on its lower surface in the form of a circular crown which will fit over hexagonal recess 16. In this case, as in the preceding case, a smooth cylindrical section 15 is provided at the crown end of the implant to allow for possible bone retraction.

The present invention has been described with particular reference to some of its specific embodiments, but it must be understood that variations and modifications may be made thereto by individuals skilled in the art without thereby departing from its scope of protection.

What is claimed is:

1. Bone fusion dental implant of substantially cylindrical shape having a crown end (3) provided with means (11, 4, 16) connecting with a prosthetic reconstruction and an apical end (2) designed to be inserted into the bone of the up per or lower jaw and made of material compatible with the bone tissues, said implant comprising an externally threaded section (6) extending from said crown end (3) over no more than one-third of the entire length of said implant and a section (1), non-threaded externally, extending from said apical end (2) over no more than two-thirds of the entire length of said implant, said threaded section being untreated and said non-threaded section being coated with a bioactive material.

2. Dental implant according to claim 1, wherein said externally threaded section (6) has no more than four flights of threads.

3. Dental implant according to claim 2, wherein said flights are self-threading.

4. Dental implant according to claim 1, wherein said connecting means includes a blind hole (11) coaxial with the implant, open toward said crown end (3) and threaded internally.

5. Dental implant according to claim 4 including, at its crown end (3), a connecting element comprised of a head (4) having the shape of a hexagon, coaxial with said blind hole (11), threaded internally and with a maximum length no greater than the diameter of said implant.

6. Dental implant according to claim 5 including, at its crown end (3), an unthreaded end section (15) with a cylindrical surface and an axial length no greater than one-eighth of the entire length of said implant.

7. Dental implant according to claim 4 including, at its crown end (3), a connecting element comprised of a recess (16) having the shape of a hexagon coaxial with said internally threaded blind hole (11).

8. Dental implant according to claim 5, in which a cylindrical flange (5) having a diameter greater than that of said implant is provided between said head (4) in the shape of a hexagon and said externally threaded section (6).

9. Dental implant according to claim 1, wherein two or more lengthwise grooves (7) are provided in said section (1) that is not threaded externally.

10. Dental implant according to claim 9,wherein said lengthwise grooves (7) have a rounded cross section and each of the two ends is rounded.

11. Dental implant according to claim 9, wherein two of said grooves (7) are diametrically opposite, terminating at their apical ends in a through hole (8) through the implant.

12. Dental implant according to claim 11, wherein said through hole (8) is circular and has rounded ends.

13. Dental implant according to claim 12, wherein the material compatible with the bone tissue is titanium or an alloy thereof.

14. Dental implant according to claim 13, wherein said section (1) that is not externally threaded and extends from said apical end (2) is coated with hydroxyapatite.

15. Dental implant according to claim 13, wherein said section (1) that is not threaded externally and extends from said apical end (2) is coated with titanium plasma.

16. Dental implant according to claim 1, wherein said apical end (2) has a hemispherical shape.

* * * * *